US009658442B2

(12) United States Patent
Geissbuehler et al.

(10) Patent No.: US 9,658,442 B2
(45) Date of Patent: May 23, 2017

(54) CUMULANT MICROSCOPY

(75) Inventors: Stefan Geissbuehler, Bern (CH);
Claudio Dellagiacoma, Renens (CH);
Matthias Geissbuehler, Lausanne (CH); Theo Lasser, Denges (CH);
Marcel Leutenegger, Chavannes (CN)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 591 days.

(21) Appl. No.: 14/126,712

(22) PCT Filed: Mar. 31, 2012

(86) PCT No.: PCT/IB2012/051581
§ 371 (c)(1),
(2), (4) Date: Feb. 19, 2014

(87) PCT Pub. No.: WO2012/172440
PCT Pub. Date: Dec. 20, 2012

(65) Prior Publication Data
US 2014/0198198 A1 Jul. 17, 2014

(30) Foreign Application Priority Data

Jun. 14, 2011 (EP) .................................... 11169880

(51) Int. Cl.
*H04N 7/18* (2006.01)
*G02B 21/36* (2006.01)
(Continued)

(52) U.S. Cl.
CPC ....... *G02B 21/365* (2013.01); *G01N 21/6408* (2013.01); *G01N 21/6458* (2013.01);
(Continued)

(58) Field of Classification Search
CPC ........... G01N 21/6458; G01N 21/6408; G02B 21/16; G02B 21/365; G02B 21/367;
(Continued)

(56) References Cited

U.S. PATENT DOCUMENTS 6,084,227 A * 7/2000 Rhoads .................... G01J 9/00
250/201.9
8,314,406 B2 * 11/2012 Ntziachristos ....... A61B 5/0073
250/458.1
(Continued)

FOREIGN PATENT DOCUMENTS

WO    WO 2010/141608    12/2010

OTHER PUBLICATIONS

European Search Report dated Oct. 26, 2011, issued in European Patent Application No. 11169880.
(Continued)

*Primary Examiner* — Nhon Diep
(74) *Attorney, Agent, or Firm* — Nixon & Vanderhye P.C.

(57) ABSTRACT

The invention describes a method and a microscopy system for imaging and analyzing stochastically and independently blinking point-like emitters. A multiple-order cumulants analysis in conjunction with an established blinking model enables the extraction of super-resolved environment-related parameter maps, such as molecular state lifetimes, concentration and brightness distributions of the emitter. In addition, such parameter maps can be used to compensate for the non-linear brightness and blinking response of higher-order cumulant images—used for example in Super-resolution Optical Fluctuation Imaging (SOFI)—to generate a balanced image contrast. Structures that otherwise would be masked by brighter regions in the conventional cumulant image become samples using spectral cross-cumulants.

11 Claims, 11 Drawing Sheets

Data acquisition

Flowchart for obtaining balanced cumulants

(51) Int. Cl.
*G01N 21/64* (2006.01)
*G02B 21/16* (2006.01)
*G02B 27/58* (2006.01)

(52) U.S. Cl.
CPC ............ *G02B 21/16* (2013.01); *G02B 21/367* (2013.01); *G02B 27/58* (2013.01)

(58) Field of Classification Search
CPC .. G02B 21/0076; G02B 21/008; G02B 27/58; G06T 2207/10056; G06T 2207/10064; G06T 3/4053; H04N 5/23232
See application file for complete search history.

(56) References Cited

U.S. PATENT DOCUMENTS

| | | | | |
|---|---|---|---|---|
| 8,488,863 B2* | 7/2013 | Boucheron | ........... | G06K 9/0014 |
| | | | | 382/131 |
| 8,625,863 B2* | 1/2014 | Enderlein | ............ | G02B 21/367 |
| | | | | 250/461.1 |
| 9,001,320 B2* | 4/2015 | Harel | ......................... | G01J 3/10 |
| | | | | 356/300 |

OTHER PUBLICATIONS

Opinion issued in European Patent Application No. 11169880.9.
Dertinger, Thomas, et al., "Achieving increased resolution and more pixels with Superresolution Optical Fluctuation Imaging (SOFI)," Optics Express, vol. 18, No. 18, Aug. 30, 2010, 11 pages, XP55010427.
Geissbuehler, Stefan, et al., "Comparison between SOFI and STORM," Biomedical Optics Express, vol. 2, No. 3, Mar. 1, 2011, 13 pages, XP55010422.
Lidke, Keith A., et al., "Superresolution by localization of quantum dots using blinking statistics," Optics Express, vol. 13, No. 18, Sep. 5, 2005, 11 pages, XP55010429.
International Search Report for PCT/IB2012/051581, mailed Aug. 21, 2012.
Foreign-language Written Opinion of the International Searching Authority for PCT/IB2012/051581, mailed Aug. 21, 2012.
Geissbuehler et al., Comparison between SOFI and STORM, Biomedical Optics Express, vol. 2, No. 3, (Mar. 1, 2011), p. 408.
Dertinger, T. et al., Achieving increased resolution and more pixels with Superresolution Optical Fluctuation Imaging (SOFI), Optics Express, vol. 18, No. 18, (Aug. 30, 2010), p. 18875.
Lidke, K.A. et al., "Superresolution by localization of quantum dots using blinking statistics", Optics Express, vol. 13, No. 18, (Jan. 1, 2005), p. 7052.
Mendel, J.M. et al., "Tutorial on higher-order statistics (spectra) in signal processing and systems theory: theoretical results and some applications", Proceedings of the IEEE, vol. 79, No. 3, (Mar. 1, 1991), pp. 278-304.
Ventalon, C. et al., "Dynamic Speckle Illumination Microscopy with Wavelet Prefiltering", Optics Leters, vol. 32, No. 11, (Jun. 1, 2007), pp. 1417-1419.

* cited by examiner

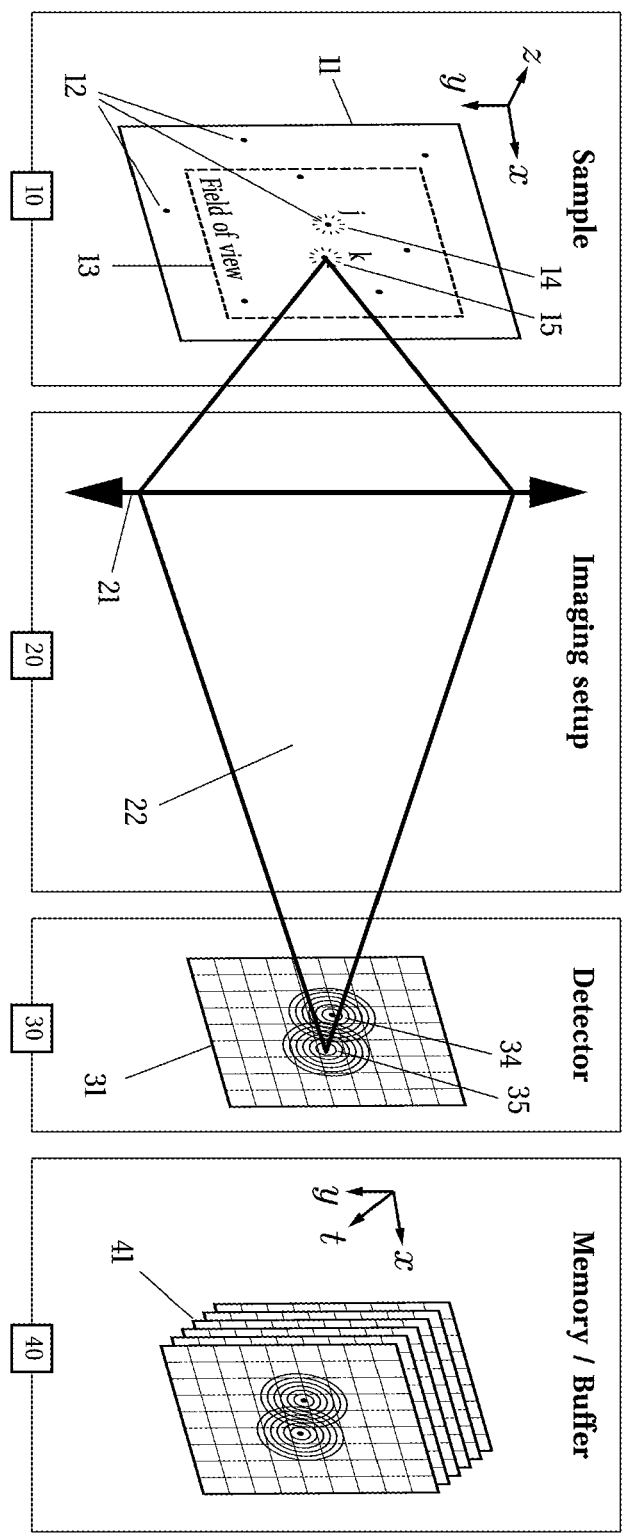
Figure 1: Data acquisition

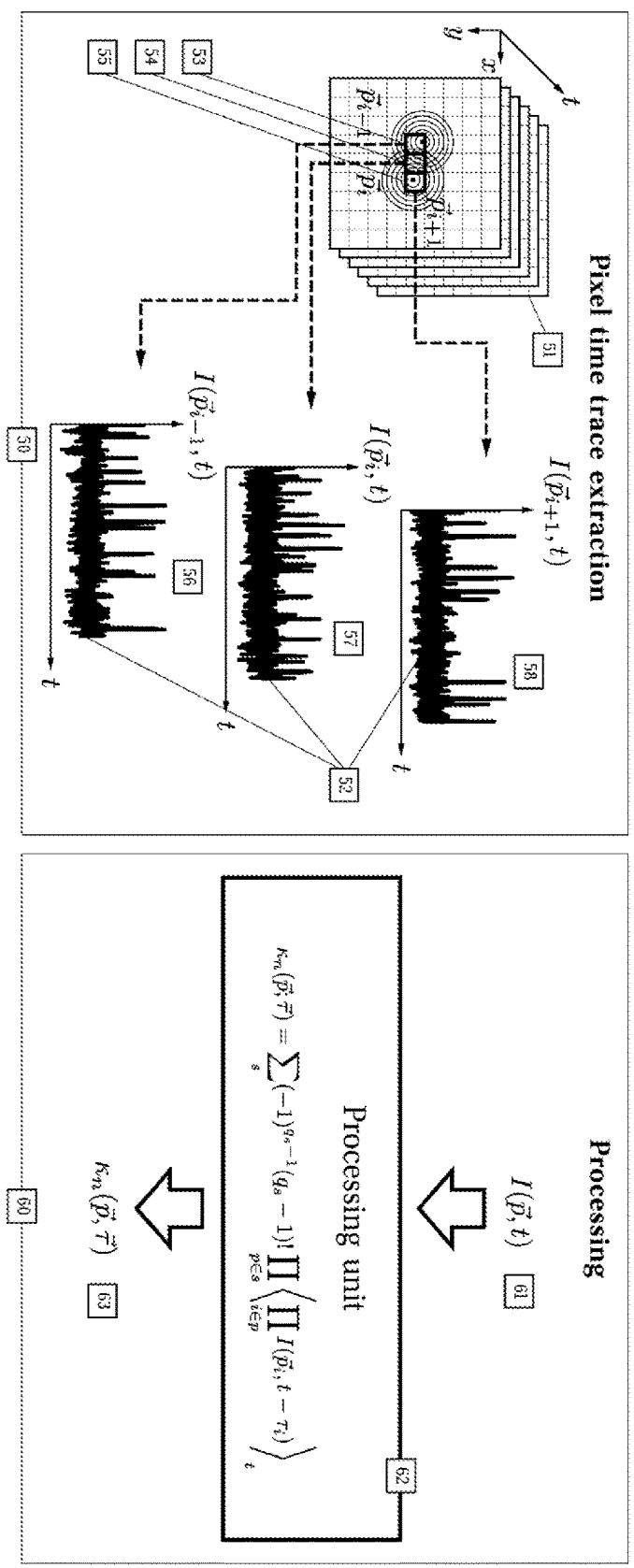
Figure 2: Cumulants computation

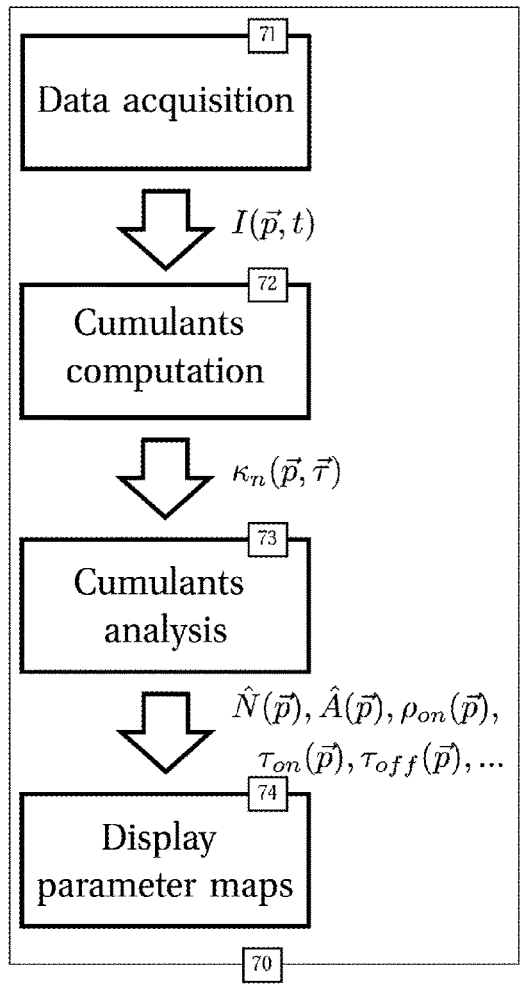
Figure 3: Flowchart for obtaining the super-resolved spatial distribution of photo-physical parameters

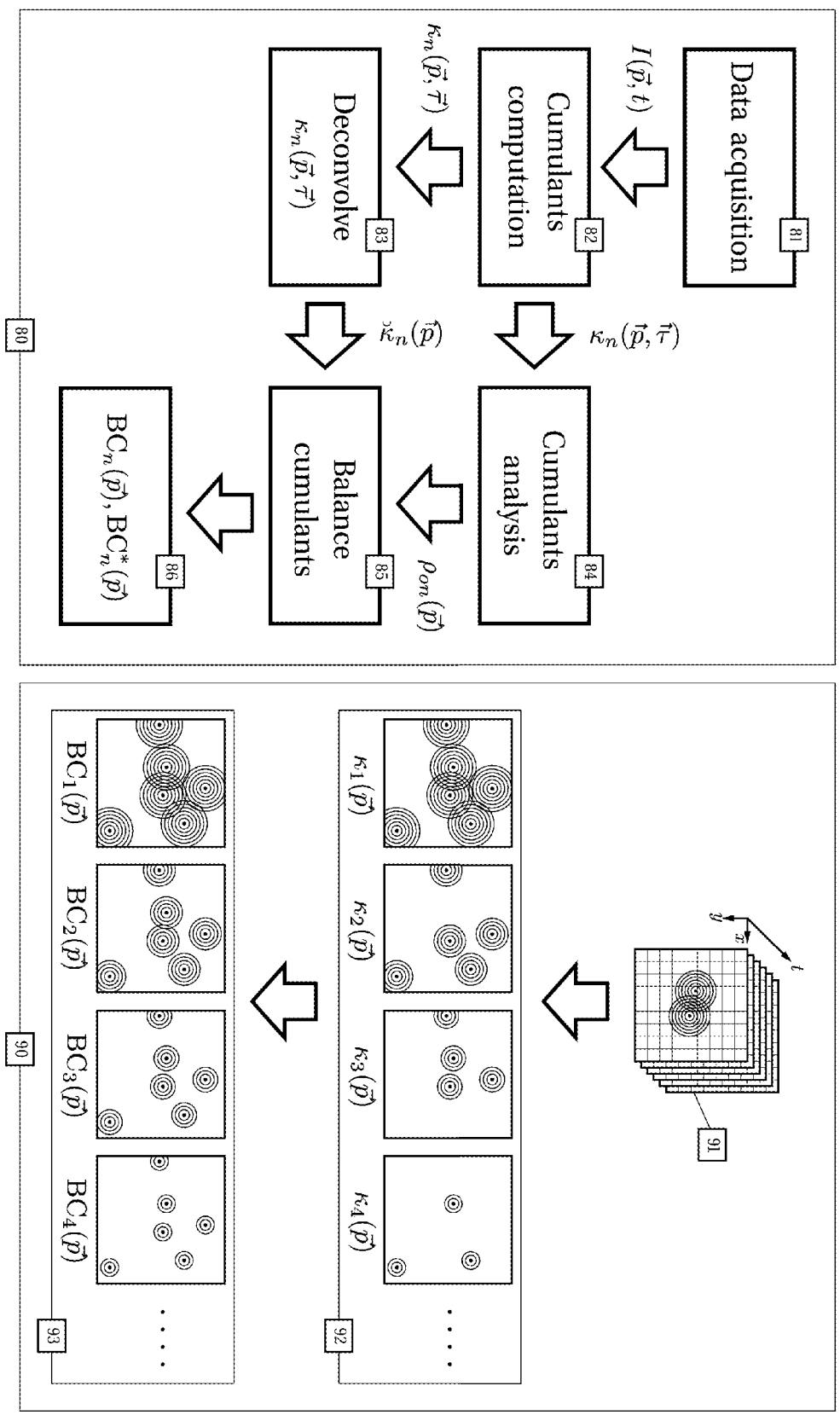
Figure 4: Flowchart for obtaining balanced cumulants

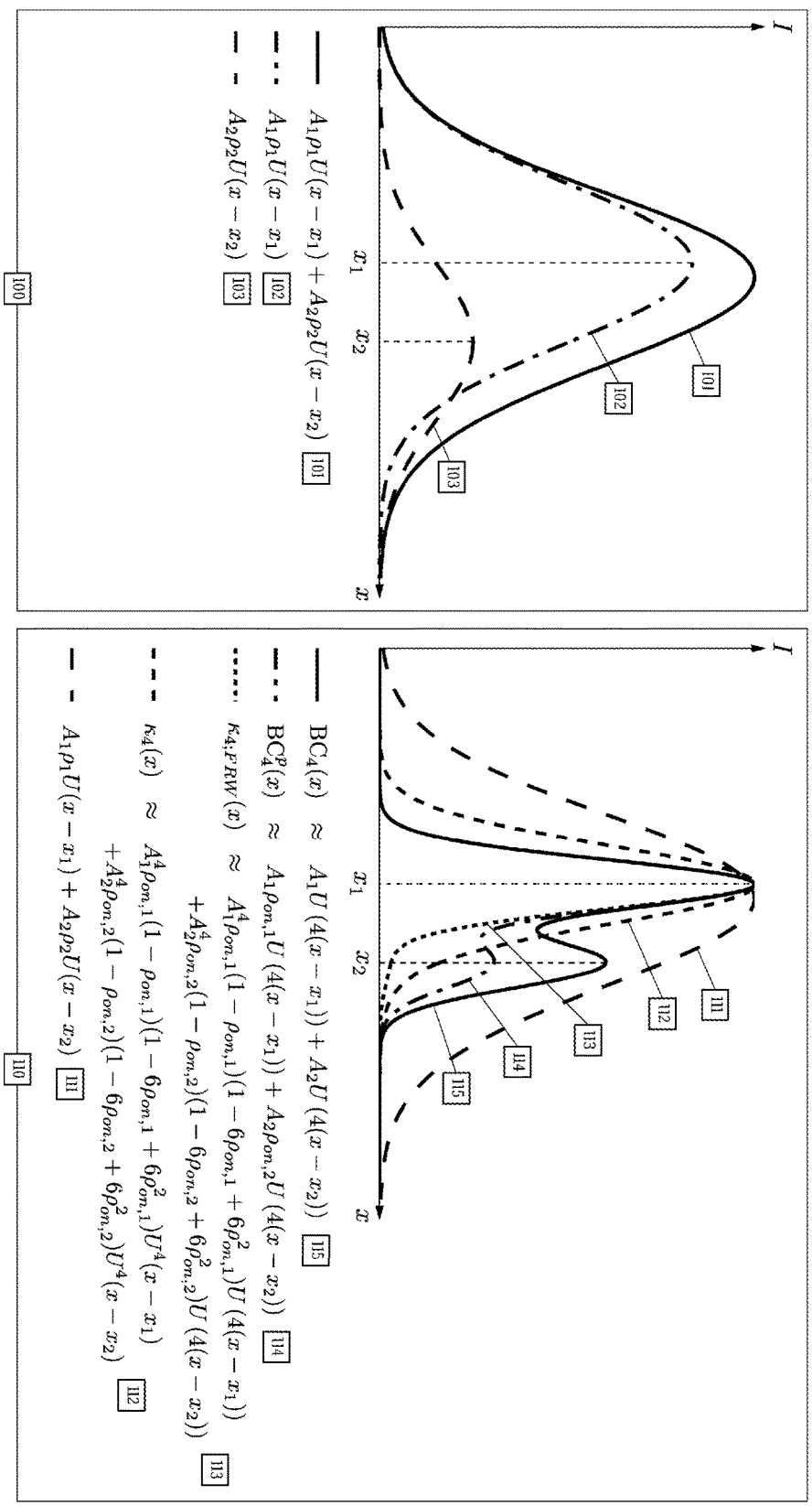
Figure 5: Illustration of balanced cumulants in comparison to unbalanced cumulants

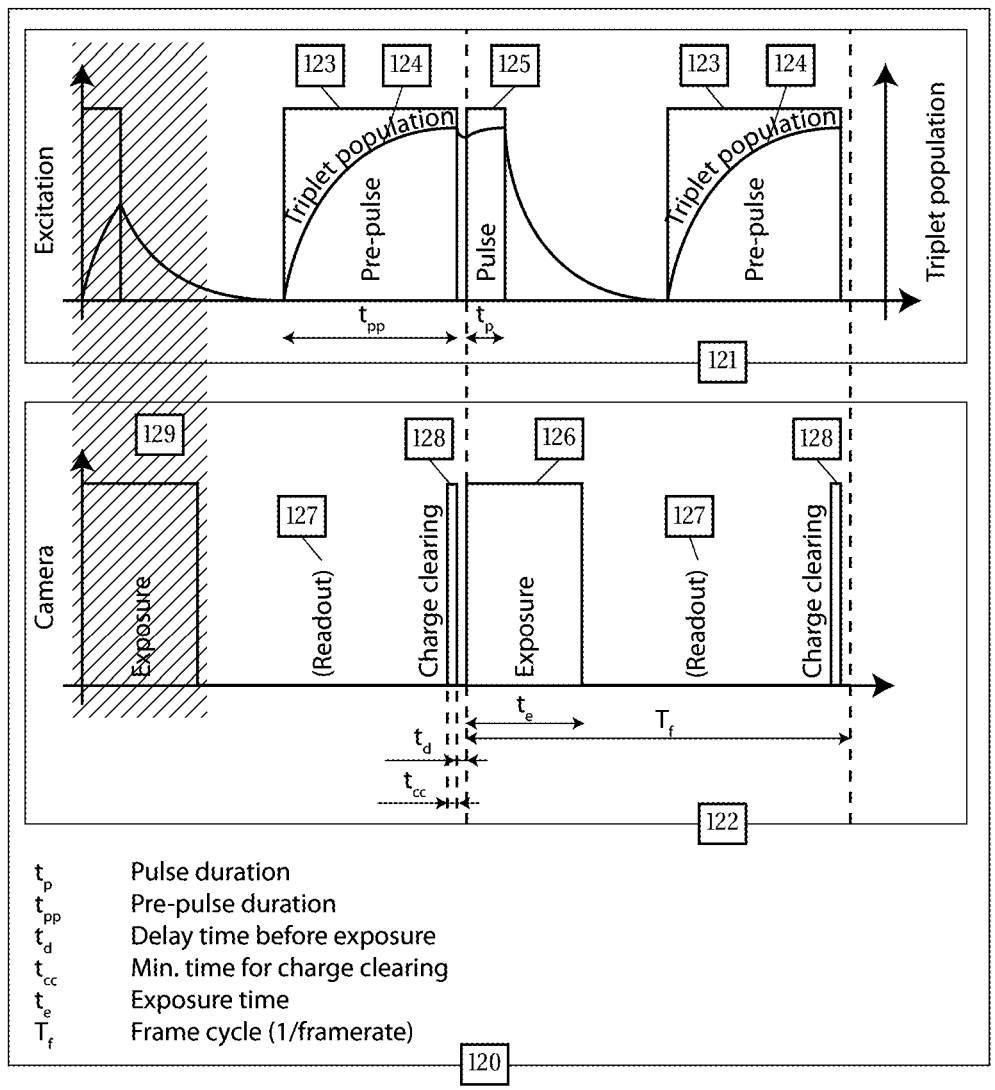
Figure 6: Modulated excitation and synchronized detection scheme for triplet cumulant microscopy

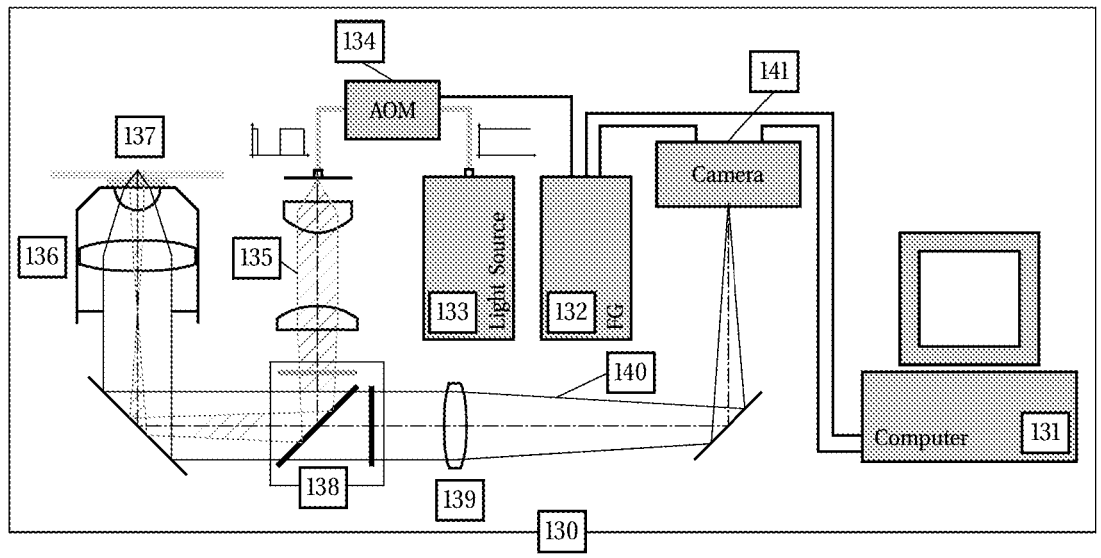
Figure 7: Example wide-field implementation of triplet cumulant microscopy

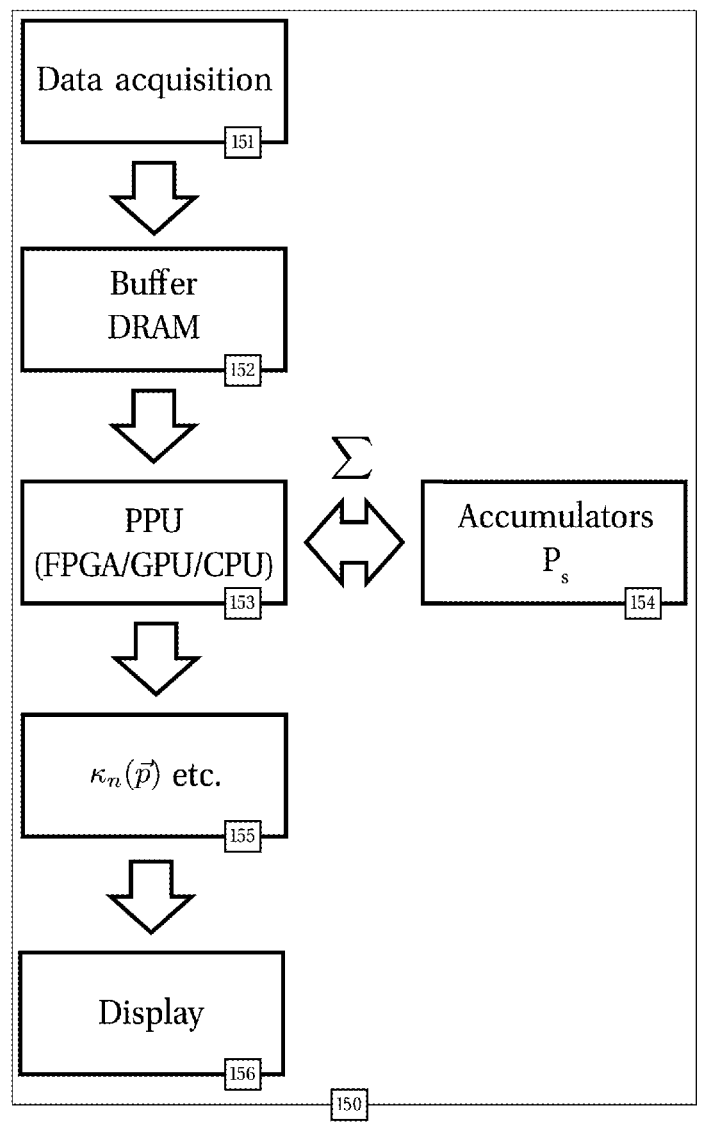
Figure 8: Flowchart for hardware implementation

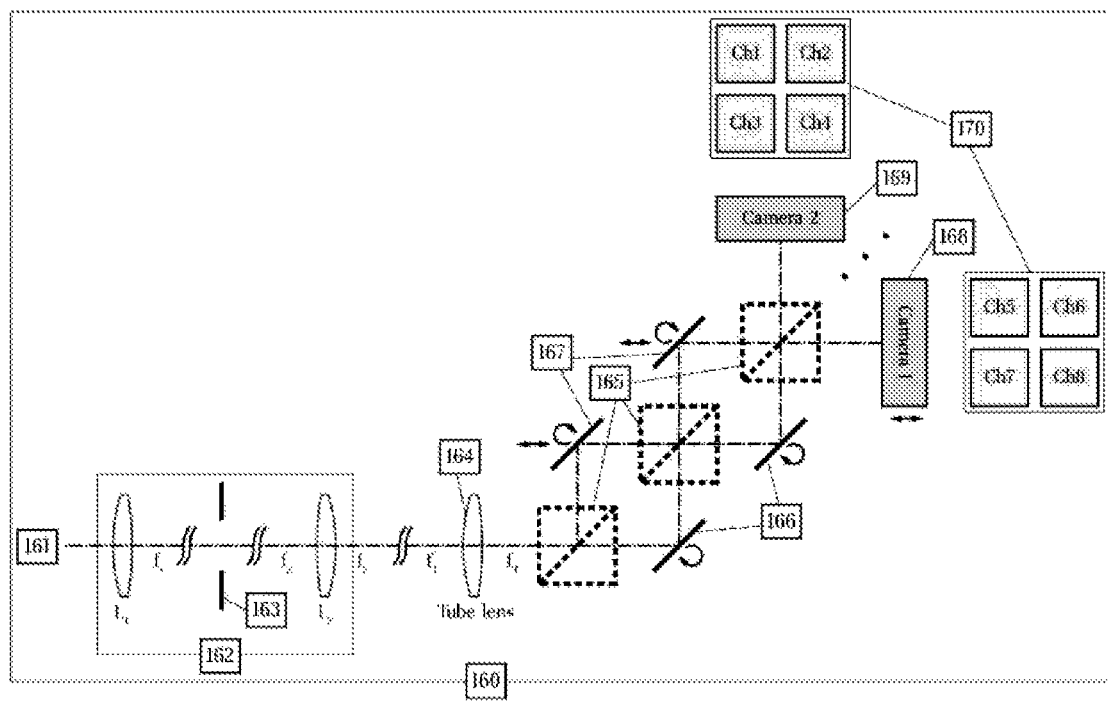
Figure 9: Multi-plane detection scheme

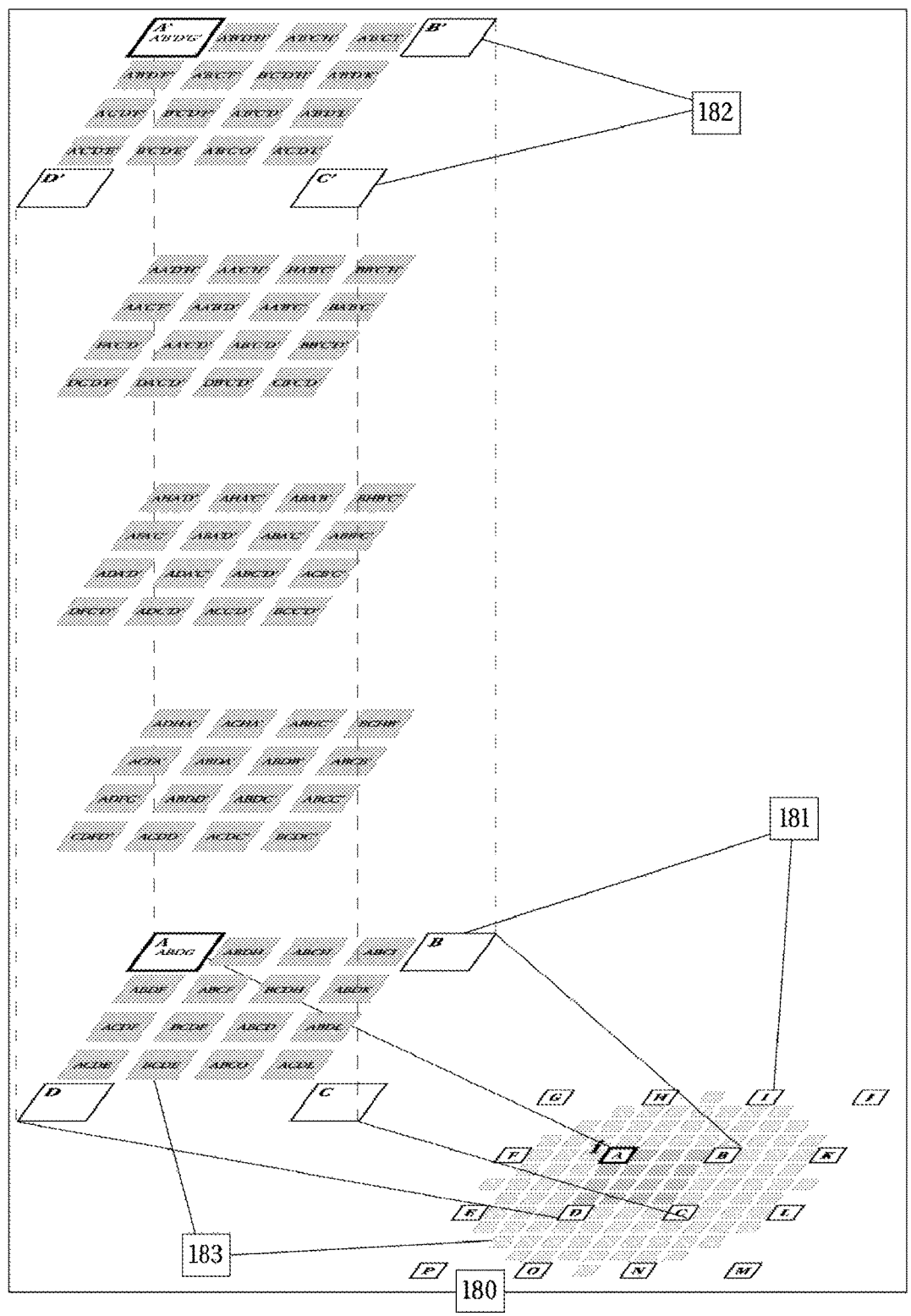
Figure 10: Example of fourth-order 3D cross-cumulant pixel combinations without repetitions

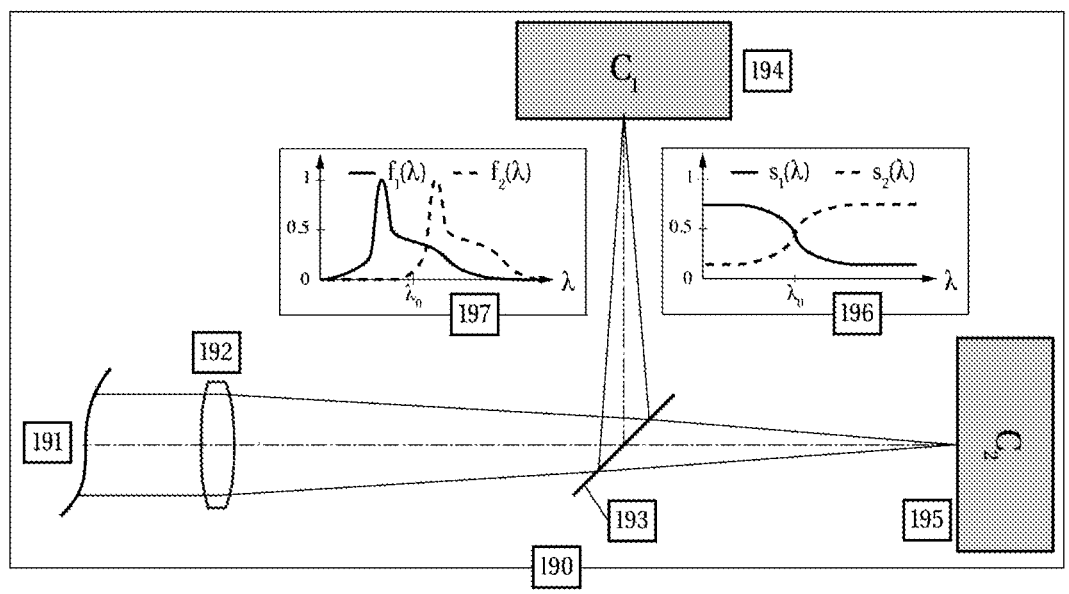
Figure 11: Example detection scheme for multi-colour cumulant microscopy

CUMULANT MICROSCOPY

This application is the U.S. national phase of International Application No. PCT/IB2012/051581, filed 31 Mar. 2012, which designated the U.S. and claims priority to EP Application No. 11169880.9, filed 14 Jun. 2011, the entire contents of each of which are hereby incorporated by reference.

FIELD OF THE INVENTION

The present invention relates to the field of super-resolution microscopy, and in particular to an improved method based on multiple-order cumulants analysis of the blinking behaviour of individual point-like emitters.

STATE OF THE ART

The references describe the background of the invention and are hereby incorporated.

The spatial resolution in optical microscopes is limited by diffraction. This so-called Abbe limit according to Abbe's theory of optical microscopy and image formation restricts the optical resolution. In this theory of image formation no further information is known of the object to be investigated. However, if object properties are known, as in fluorescence microscopy, where the fluorescent labels are emitting light in a known statistical manner, with an emitter size well below the diffraction limit, a higher resolution can be achieved by exploiting saturation effects or utilizing stochastic blinking to identify and localize single emitters. These new imaging concepts are known as super-resolution microscopy.

During the last two decades, several new imaging concepts overcoming the diffraction limit have been disclosed and filed:

STED as described for example in the U.S. Pat. No. 5,731,588, U.S. Pat. No. 7,719,679, U.S. Pat. No. 7,538,893, U.S. Pat. No. 7,430,045, U.S. Pat. No. 7,253,893, U.S. Pat. No. 7,064,824 with the demand for a special optical imaging instrumentation, a limited acquisition time mainly due to the known limitations of an image scanning device and the requirement for strong excitation sources in order to achieve super-resolution with a good imaging contrast.

SIM; SSIM; I5M; as described for example in the U.S. Pat. No. 5,671,085 with a demonstrated super-resolution due to structured illumination based on a rather complicated optical setup and the necessity to extract the improved resolution by combining several images acquired with a phase controlled illumination sequence.

PALM as well as STORM as described for example in the U.S. Pat. No. 7,710,563, U.S. Pat. No. 7,626,703, U.S. Pat. No. 7,626,695, U.S. Pat. No. 7,626,694, U.S. Pat. No. 7,535,012 are based on a widefield fluorescence microscopy concept exploiting the stochastic blinking of individual fluorophores. These methods impose stringent requirements on the labeling density along with meta-stable dark-states of the fluorophores versus high brightness in the fluorescent state. Both methods require rather long acquisition times for recording thousands of images. However, illumination or sample induced stochastic switching of fluorophores followed by localization proved to be an innovative concept with a substantial resolution enhancement demonstrated for two-dimensional (2D) images. Three-dimensional (3D) localization microscopy usually needs a modification of the optical setup. Furthermore, many of the proposed solutions are suffering from a rather limited depth of field and are limited due to background radiation originating from unresolved and out-of-focus sample structures.

Lidke et al. published in 2005 (Optics Express 2005, Vol. 13, pp. 7052-7062) a novel imaging concept based on Independent Component Analysis (ICA) and the blinking statistics of quantum dots (QDs) allowing for the separation and localization of overlapping diffraction patterns. However, for a successful localization, an estimation of the number of QDs is needed and the position accuracy is substantially influenced by an under- or overestimation of the number of emitters.

SOFI as described in the patent PCT/US2010/037099 represents a new super-resolved imaging concept, which exploits the statistical blinking behaviour of the fluorescent biomarkers without any prior knowledge of emitters within a diffraction-limited spot. SOFI is based on a pixel-wise auto- or cross-cumulant analysis, which yields a resolution enhancement that grows with the cumulant order in all three dimensions. Uncorrelated noise, stationary background as well as out-of-focus light are greatly reduced by the cumulant analysis. Hence, the step from two- to three-dimensional imaging is facilitated and can be easily realized in a so-called z-stacking, i.e. the sequential imaging of depth slices, well known in classical and confocal microscopy. 2D and 3D imaging can be performed with a classical widefield or confocal microscope. Acquiring multiple image sequences of blinking fluorophores and applying the pixel-wise cumulant analysis in a post processing is sufficient to generate super-resolved 3D images. The main drawback of SOFI is the amplification of heterogeneities in molecular brightness and photo-kinetics, which limits the use of higher-order cumulants.

At the exception of STED, all mentioned super-resolution techniques provide structural information only. The blinking behaviour is not evaluated further even though it might provide physically meaningful parameters that may be linked to microenvironment properties and thereby report functional information.

There is still an important need for an imaging concept providing super-resolution along with functional information, high contrast, a potential for fast imaging, intrinsic 3D capability, live-cell suitability, and compatibility with commercially available microscopes.

GENERAL DESCRIPTION OF THE INVENTION

An objective of the invention is to solve at least the above-mentioned problems and/or disadvantages and to provide the advantages described herewith in the following.

The invention aims to use higher-order statistics for characterizing the blinking kinetics of single point-like emitters and estimate the spatial distribution of molecular brightness and density to extract microenvironment-related properties with super-resolution.

Another objective of the invention is to correct for the resulting brightness imbalance of cumulant-based super-resolution yielding an improved contrast and revealing hidden structural information.

Further on, the invention describes the possibility of combining the complementary cumulant- and localization-based super-resolution techniques to increase their applicability and overall performance.

Another objective is to expand the range of suitable probes for blinking-based super-resolution microscopy by the use of illumination-induced fluctuations with a (saturated) structured excitation such as a speckle field, or the use of a modulated excitation along with synchronized detection to populate and sense the fast triplet state fluctuations.

Another objective is to perform super-resolved multi-colour, colocalization, FRET and anisotropy analysis by using cross-cumulants in different spectral and/or polarization channels.

The above-cited objectives are achieved with the present invention, which concerns a method and a microscopy system as defined in the claims.

Additional advantages, objects and features of the invention will be set forth in the following chapters.

DEFINITIONS, TERMS AND ELEMENTS

"Point-like emitter": Small particle (with respect to the point-spread function) that absorbs, reemits or scatters photons.

"Stochastic blinking": A fluctuation in measurable optical properties (e.g. emission, absorption or scattering) between at least two states of the point-like emitter. It can be intrinsic or provoked by external means and has to be independent among the individual emitters. For example, the fluctuation can be caused by a transition between two or more molecular energy levels or by a reorientation or conformational change.

"Parameter map": Image or volume rendering encoding the spatial distribution of an estimated physical quantity.

"Microenvironment": Local concentration of a certain molecular species or the strength of a property of the medium in vicinity to a point-like emitter.

BRIEF DESCRIPTION OF THE DRAWINGS

FIG. 1: Data acquisition
FIG. 2: Cumulants computation
FIG. 3: Flowchart for obtaining the super-resolved spatial distribution of photo-physical parameters
FIG. 4: Flowchart for obtaining balanced cumulants
FIG. 5: Illustration of balanced cumulants in comparison to unbalanced cumulants
FIG. 6: Modulated excitation and synchronized detection scheme for triplet cumulant microscopy
FIG. 7: Example wide-field implementation of triplet cumulant microscopy
FIG. 8: Flowchart for hardware implementation
FIG. 9: Multi-plane detection scheme
FIG. 10: Example of fourth-order 3D cross-cumulant pixel combinations without repetitions
FIG. 11: Example detection scheme for multi-colour cumulant microscopy

DETAILED DESCRIPTION OF THE INVENTION

The present invention describes a method for imaging and analysing a field-of-view composed of stochastically and independently blinking point-like emitters.

The acquisition procedure and the hardware requirements are similar to those described in the SOFI patent PCT/US2010/037099. An optical imaging system (microscope, telescope, etc.) is used to acquire the above mentioned field-of-view repeatedly (over time) in wide-field or confocal detection. The blinking signals emanating from individual point-like emitters are blurred by the point-spread function (PSF, impulse response) of the optical system and recorded on a set of detection elements (pixels) as a function of time. The extent of the PSF shall only be limited by diffraction and optical aberrations in the detection arm. Therefore, the PSF shall spread over several pixels. The instrumentation has to be suited and sensitive enough to detect the stochastic blinking of the emitter in time and space.

FIG. 1 shows schematically the signal acquisition process in wide-field detection. The system is subdivided in the sample space 10, the microscope system 20 (schematically) and the detector space 30 containing an array detector 31. The sample space 10 shows a selected 2D sample plane 11, containing several point-like emitters 12 located in said sample plane 11. The microscope system 20, represented by the imaging elements 21, provides images of point-like emitters inside the field of view 13. In general the microscope system 20 can only access point-like emitters, which are emitting light (14, 15). The distance between the emitters 14, 15 is below the resolution limit set by the PSF size. Therefore the corresponding images 34, 35 captured by the array detector 31 show overlapping unresolved blurred spots. A time series of captured and memorized images 41 contains the data corresponding to the captured images/spots of the stochastically blinking point-like emitters. The memory buffer 40 contains sufficiently long registered data sets used for the following cumulant analysis.

Similarly to SOFI, the acquired pixel time traces are extracted and processed by calculating higher-order (cross-) cumulants, with or without time lags. In the most general sense, the cumulant of order n of a pixel set $P=\{\vec{p}_1, p_2, \ldots, \vec{p}_n\}$ with time lags $\vec{\tau}=[\tau_1, \tau_2, \ldots, \tau_n]$ can be calculated according to Leonov and Shiryaef (Theory Probab. Appl. (1959) vol. 4 (3) pp. 319-329) as $$\kappa_n\left(\vec{p} = \frac{1}{n}\sum_{i=1}^{n}\vec{p}_i; \vec{\tau}\right) = \sum_s (-1)^{q_s-1}(q_s-1)!\prod_{p\in s}\left\langle \prod_{i\in p} I(\vec{p}_i, t-\tau_i)\right\rangle_t,$$

where $\langle \ldots \rangle_t$ stands for averaging over the time t, s runs over all partitions of the set $S=\{1, 2, \ldots, n\}$, p enumerates the $q_s$ subsets or parts of partition s and $I(\vec{p},t)$ is the intensity distribution measured over time on a detector pixel $\vec{p}$.

FIG. 2 illustrates the different steps for computing higher-order cumulants from the acquired images 41. The data 51 contained in the memory buffer 40, corresponds to the captured light intensities of the point-like emitters. The intensity time traces of pixels 53, 54, 55 are indicated in 56, 57, 58. These representative pixel traces 52 are the input elements 61 for the cumulant-processing unit 62, calculating the n-th order cumulant 63 according to the preceding paragraph.

As a consequence of additivity, the cumulant of a sum of independent random variables (e.g. independently blinking point-like emitters) corresponds to the sum of the cumulants of each individual random variable. The intensity distribution $I(\vec{p},t)$ of a sample composed of N independently fluctuating point-like emitters can be written as $$I(\vec{p}, t) = \sum_{k=1}^{N} A_k U(\vec{p}-\vec{r}_k)s_k(t) + b(\vec{p})$$

where $A_k$, $\vec{r}_k$ and $s_k$ denote the emitter's brightness, position and normalized temporal fluctuation signal, U(r) is the system's PSF and b represents a temporally constant background term. Taking the n-th order cumulant leads to $$\kappa_n\{I(\vec{p},t)\} = \sum_{k=1}^{N} \kappa_n\{A_k U(\vec{p}-\vec{r}_k)s_k(t)\} + \kappa_n\{b(\vec{p})\} =$$

$$\sum_{k=1}^{N} A_k^n U^n(\vec{p}-\vec{r}_k)\omega_{n,k} + \begin{cases} b(\vec{p}) & n=1 \\ 0 & n>1 \end{cases}$$

with $\omega_{n,k} = \kappa_n\{s_k(t)\}_t$ a weighting factor depending on the characteristic blinking properties of the emitter k. If we approximate $U(r)$ by a Gaussian function, $U^n(r)$ yields again a Gaussian function with a $\sqrt{n}$-fold reduced size in all dimensions leading to a in $\sqrt{n}$-fold improved resolution.

Apart from the super-resolved structural information revealed by higher-order cumulants, the weighting factors $\omega_{n,k} = \kappa_n\{s_k(t)\}_t$ also contain exploitable information concerning the photo-physics of each emitter, which can be extracted by considering multiple cumulant orders. In the simplest case, the emitter fluctuates between two states (corresponding to a Bernoulli distribution), a bright state $S_{on}$ and a dark state $S_{off}$. The relative amount of time it stays in the state $S_{on}$ and $S_{off}$, respectively, can be defined as $$\rho_{on} = \frac{\tau_{on}}{\tau_{on}+\tau_{off}}, \rho_{off} = \frac{\tau_{off}}{\tau_{on}+\tau_{off}} = 1 - \rho_{on},$$

where $\tau_{on}$ and $\tau_{off}$ off are the lifetimes of the states $S_{on}$ and $S_{off}$. We define the normalized temporal fluctuation signal $s_k(t)$ to be 1 when the emitter is in the state $S_{on}$ and $\epsilon \in [0,1)$ when it is in the state $S_{off}$. The weighting factors $\omega_{n,k}$ of the first four orders become then $$\omega_{1;k} = (1-\epsilon_k)\rho_{on,k}$$
$$\omega_{2;k} = (1-\epsilon_k)^2 \rho_{on,k}(1-\rho_{on,k})$$
$$\omega_{3;k} = (1-\epsilon_k)^3 \rho_{on,k}(1-\rho_{on,k})(1-2\rho_{on,k})$$
$$\omega_{4;k} = (1-\epsilon_k)^4 \rho_{on,k}(1-\rho_{on,k})(1-6\rho_{on,k}+6\rho_{on,k}^2)$$
$$\vdots$$
$$\omega_{n;k} = (1-\epsilon_k)^n f_n(\rho_{on,k}),$$

with $$f_n(\rho_{on,k}) = \rho_{on,k}(1-\rho_{on,k})\frac{\partial f_{n-1}}{\partial \rho_{on,k}}$$

the n-th order cumulant of a Bernoulli distribution with probability $\rho_{on,k}$. Since parameters, such as the molecular state lifetimes and the molecular brightness depend on the local environment, the oxygen concentration influences the dark-state lifetime of organic fluorophores for instance, we assume region-dependent but locally constant on-time ratios and amplitudes. The overall cumulants may then be approximated by $$\kappa_1(\vec{p}) = \hat{A}(\vec{p})\rho_{on}(\vec{p})\sum_{k=1}^{N} U(\vec{p}-\vec{r}_k) + b(\vec{p}) \approx \hat{A}(\vec{p})\hat{N}(\vec{p})E\{U(\vec{p})\}\rho_{on}(\vec{p}) + b(\vec{p})$$

$$\kappa_2(\vec{p}) \approx \hat{N}(\vec{p})\hat{A}^2(\vec{p})E\{U^2(\vec{p})\}\rho_{on}(\vec{p})(1-\rho_{on}(\vec{p}))$$

-continued $$\kappa_3(\vec{p}) \approx \hat{N}(\vec{p})\hat{A}^3(\vec{p})E\{U^3(\vec{p})\}\rho_{on}(\vec{p})(1-\rho_{on}(\vec{p}))(1-2\rho_{on}(\vec{p}))$$

$$\kappa_4(\vec{p}) \approx \hat{N}(\vec{p})\hat{A}^4(\vec{p})E\{U^4(\vec{p})\}\rho_{on}(\vec{p})(1-\rho_{on}(\vec{p}))(1-6\rho_{on}(\vec{p})+6\rho_{on}^2(\vec{p}))$$

$$\vdots$$

$$\kappa_n(\vec{p}) \approx \hat{N}(\vec{p})\hat{A}^n(\vec{p})E\{U^n(\vec{p})\}f_n(\rho_{on};\vec{p}),$$

where $E\{\ldots\}$ is the expectation operator. For a Gaussian PSF, the n-th order moment can be written as $$E\{U^n(\vec{p})\} \cong \frac{c(\sigma_{xy},\sigma_z)}{n^{3/2}},$$

with $c(\sigma_{xy},\sigma_z)$ a constant depending on the spatial extent of the PSF. Finally, we can write $$\kappa_n(\vec{p}) \approx \frac{c}{n^{3/2}}\hat{N}(\vec{p})\hat{A}^n(\vec{p})f_n(\rho_{on};\vec{p})$$

which then enables the pixel-wise estimation of the parameters $\hat{N}(\vec{p})$, $\hat{A}(\vec{p})$ and $\rho_{on}(\vec{p})$ by considering three or more cumulant orders.

To estimate the parameters of a two-state system assuming a Gaussian PSF, cumulant orders two to four can be used to build the ratios $$K_1(\vec{p}) = \frac{3^{3/2}\kappa_3}{2^{3/2}\kappa_2}(\vec{p}) = \hat{A}(\vec{p})[1-2\rho_1(\vec{p})]$$

$$K_2(\vec{p}) = \frac{4^{3/2}\kappa_4}{2^{3/2}\kappa_2}(\vec{p}) = \hat{A}^2(\vec{p})[1-6\rho_1(\vec{p})+6\rho_1^2(\vec{p})]$$

and to solve for the amplitude $$\hat{A}(\vec{p}) = \sqrt{3K_1^2(\vec{p})-2K_2(\vec{p})},$$

the on-time ratio $$\rho_{on}(\vec{p}) = \frac{1}{2} - \frac{K_1(\vec{p})}{2\hat{A}(\vec{p})}$$

and the number of particles $$N(\vec{p}) = \frac{\kappa_2(\vec{p})}{\hat{A}^2(\vec{p})\rho_{on}(\vec{p})[1-\rho_{on}(\vec{p})]}.$$

The spatial resolution of the estimation is given by the lowest order cumulant, i.e. the second order in the outlined example. However, the presented solution is not unique. In principle, any three distinct cumulant orders could have been used to provide a solution by solving the equation system or using a fitting procedure. Furthermore, the method is not limited to a two-state system; it can be extended to a multi-state system (for example a decreased emission due to an energy transfer to an acceptor approaching the emitter), as long as their differences can be detected with the imaging setup.

If in addition the cumulants are computed for different sets of time lags and the acquisition rate oversamples the blinking rate, it is also possible to extract absolute estimates on the characteristic lifetimes of the different states. In a two-state system, using the second order cumulant for example, which is equivalent to a centred second order correlation, it is sufficient to measure the temporal extent of the correlation curve before it approaches zero to get an estimate on the blinking period. The lifetimes of the on- and off-state can be calculated easily from the estimated on-time ratio and the blinking period.

The flowchart 70 in FIG. 3 summarizes the different steps involved for obtaining the parameter maps $\hat{N}(\vec{p})$, $\hat{A}(\vec{p})$, $\rho_{on}(\vec{p})$, $\tau_{on}(\vec{p})$ and $\tau_{off}(\vec{p})$ as described and indicated by the formulas above. For displaying the parameter maps 74, one can for example use a colour coding of the parameter values and overlay a cumulant or balanced cumulant (as described in the following paragraphs) image of any order as an alpha or transparency map, in order to suppress arbitrary parameter estimations in the background of the sample.

Embodiment 1

Balanced Cumulants

Computing higher-order cumulants for structural super-resolution microscopy amplifies heterogeneities in molecular brightness and blinking. As described in paragraphs above, the underlying molecular photo-physics can be extracted by combining the information of several cumulant orders, which allows correcting the resulting amplified heterogeneities and retrieving hidden information.

As shown in paragraphs above, the n-th order cumulant of independently blinking emitters may be approximated by $$\kappa_n(\vec{p}) \approx \hat{A}^n(\vec{p}) f_n(\rho_{on}; \vec{p}) \sum_{k=1}^{N} U^n(\vec{p} - \vec{r}_k)$$

$$\approx \hat{A}^n(\vec{p}) f_n(\rho_{on}; \vec{p}) \sum_{k=1}^{N} \delta(\vec{p} - \vec{r}_k) * U^n(\vec{p})$$

FIG. 4 shows a flowchart for computing balanced cumulants (80). After data acquisition 81 and cumulant computation 82 as described in paragraph, $\kappa_n(\vec{p})$ is spatially deconvolved with any suitable algorithm 83, for example by using Wiener filtering:

$$\check{\kappa}_n(\vec{p}) = F^{-1} \left\{ F\{\kappa_n(\vec{p})\} \cdot \frac{(F\{U^n(\vec{p})\})^*}{(F\{U^n(\vec{p})\})^* F\{U^n(\vec{p})\} + \alpha} \right\}, \alpha \ll 1,$$

where $F\{\ldots\}$ and $F^{-1}\{\ldots\}$ denote the forward and inverse Fourier transforms, and $\alpha$ is a regularization constant to avoid a division by zero. As a result, we would obtain ideally $$\check{\kappa}_n(\vec{p}) \approx \hat{A}^n(\vec{p}) f_n(\rho_{on}; \vec{p}) \sum_{k=1}^{N} \delta(\vec{p} - \vec{r}_k).$$

This intermediate deconvolution step is needed to correct for the heterogeneities without compromising on spatial resolution.

In parallel to the deconvolution, a combination of different cumulant orders is used to estimate the on-time ratio $\rho_{on}(\vec{p})$ 84 as described in paragraphs above and to calculate $f_n(\rho_{on}; \vec{p})$. Using the deconvolved cumulant $\check{\kappa}_n(\vec{p})$ and the polynomial $f_n(\rho_{on}; \vec{p})$, we can calculate brightness balanced cumulants (BC) with a linear response to the molecular brightness or photon balanced cumulants ($BC^p$) with a linear response to the amount of photons collected 85, according to $$BC_n(\vec{p}) = \sqrt[n]{\frac{\check{\kappa}_n(\vec{p})}{\text{sgn}\{f_n(\rho_{on}; \vec{p})\}(|f_n(\rho_{on}; \vec{p})| + \beta)}} * U^n(\vec{p}), \beta \ll 1,$$

respectively $$BC_n^p(\vec{p}) = \sqrt[n]{\frac{\check{\kappa}_n(\vec{p})}{\text{sgn}\{f_n(\rho_{on}; \vec{p})/\rho_{on}(\vec{p})\}(|f_n(\rho_{on}; \vec{p})/\rho_{on}(\vec{p})| + \beta)}} * U^n(\vec{p}),$$

$$\beta \ll 1.$$

The result of the division of the deconvolved cumulant $\check{\kappa}_n(\vec{p})$ by the polynomial $f_n(\rho_{on}; \vec{p})$, respectively $f_n(\rho_{on}; \vec{p})/\rho_{on}(\vec{p})$ should be positive everywhere. Negative values arise from artefacts and hence can be truncated. It should be noted, that this division might amplify structural artefacts in regions of low signal-to-noise ratios (i.e. where $f_n(\rho_{on}; \vec{p})$ is close to 0). However, since the roots of $f_n(\rho_{on}; \vec{p})$ are distinct for every n, these regions can be easily replaced with the result from the balanced cumulant order n−1 or n+1, which then results in a better overall image quality. The reconvolution with the PSF raised to the power of n after the linearization is optional, but recommended in order to minimize the amount of introduced image artefacts.

The right part (90) of FIG. 4 illustrates the effect of heterogeneous amplitude and/or on-time ratio distributions on the resulting cumulant orders 1 to 4 (92) with a selective amplification of some of the emitters and how the balanced cumulants 93 can retrieve the attenuated emitters. The brightness-balanced cumulants can be interpreted as the sum of the individual molecular amplitudes convolved by the PSF raised to the power of n $$BC_n(\vec{p}) \approx \sum_{k=1}^{N} A_k \delta(\vec{p} - \vec{r}_k) * U^n(\vec{p})$$

$$\approx \sum_{k=1}^{N} A_k U^n(\vec{p} - \vec{r}_k),$$

whereas the photon balanced cumulants additionally involve the on-time ratio $$BC_n^p(\vec{p}) \approx \sum_{k=1}^{N} A_k \rho_{on,k} U^n(\vec{p} - \vec{r}_k).$$

Since the cumulant equivalent optical transfer function (cOTF) corresponds to an n-fold convolution of the imaging system's OTF, the support of the cOTF, respectively the cut-off spatial frequency, scales linearly with the order n. By applying a simple reweighting scheme in the Fourier domain of the n-th order cumulant, a final resolution improvement that scales almost linearly with n can be achieved (see Dertinger et al., Opt. Express 2010):

$$\kappa_{n;FRW}(\vec{p}) = F^{-1}\left\{\frac{F\{\kappa_n(\vec{p})\}F\{U(n\vec{p})\}}{F\{U^n(\vec{p})\}+\gamma}\right\}, \gamma \ll 1.$$

Accordingly for balanced cumulants, instead of convolving with $U^n(\vec{p})$ (see above paragraph), it is also possible to convolve with the n-times size-reduced PSF $U(n\vec{p})$, without significantly pronouncing non-physical artefacts.

FIG. 5 shows a 1D example comparing unbalanced and balanced cumulants of two emitters located at $x_1$ and $x_2$ with amplitudes 1 and 0.6 and on-time ratios 0.5 and 0.25. The left part 100 illustrates the mean intensity distribution observed on a detector 101, which corresponds to the sum of the time-averaged responses of each emitter 102,103 being the emitters' amplitudes times the respective on-time ratios and the system's PSF. The right part 110 illustrates the results of the balanced and unbalanced cumulants. The curve 111 corresponds to the first order cumulant, or the mean image, curves 112 and 113 represent the unbalanced cumulant of order 4 without, respectively with Fourier reweighting and 114, 115 show the photon, respectively brightness balanced cumulants ($BC^p$, BC), which reveal the presence of emitter 2.

Embodiment 2

Cumulant Microscopy Combined with Single Molecule Localization

The estimation of the on-time ratio and the labelling density is crucial for single molecule localization with a minor percentage of false localizations. Cumulant microscopy can provide an estimate on the spatial distribution of these parameters (see above), which in turn can be used to perform single molecule localization in regions with suitable on-time ratios and labelling densities, whereas in the other regions the cumulant image is used for providing more details.

Embodiment 3

Microenvironment Sensitive Imaging

As mentioned above, fluorescence blinking is highly sensitive to the chemical microenvironment. For example, if the observed blinking is due to cycling between the singlet states (bright state) and the excited triplet state of a fluorophore or any other state mediated by the triplet state (dark state), the on-time ratio is highly influenced by the concentration of triplet state quenchers, like for example oxygen. Oxygen in its normal form is in a triplet state and upon collision with a fluorophore being in its excited triplet state, an energy transfer may happen, transforming the fluorophore back to its fundamental ground state and oxygen to an excited and highly reactive singlet state. The presence of oxygen thus reduces the dark state lifetime and accordingly increases the on-time ratio, which therefore could be used as an oxygen sensor.

If reducing or oxidizing agents are present, there exist alternative relaxation pathways from excited states of fluorophores that may influence the blinking behaviour. For example, cells are highly complex systems with many different local environments and organelles. A spatially super-resolved statistical analysis of the molecular blinking provides additional information, which might be used to deduce some of the properties (chemical, temperature, pressure, local pH, etc.) of the surrounding microenvironments and thus help for a better understanding of biological processes at a subcellular level.

Embodiment 4

Functional Super-Resolution Microscopy Exploiting Triplet Blinking

Ideal probes for cumulant microscopy are bright and provide many blinking cycles. Nonetheless, the required minimum number of detected photons in a bright state can be much lower than for localization-based techniques, in the order of tens of photons per molecule and on-state lifetime (see Geissbuehler et al., Biomed. Opt. Express 2011). Therefore, the fast stochastic blinking of fluorophores induced by cycling between the bright singlet states and the dark excited triplet state should already yield sufficient photons per cycle to perform cumulant microscopy.

The triplet state is common to almost all fluorophores, has a typical lifetime of about 1000 times the corresponding singlet lifetime and results in a non-radiative relaxation or weak phosphorescence. However, the triplet state excitation and relaxation is usually too fast to be captured by a state-of-the-art microscopy camera and the fluctuations are averaged out. In order to overcome the speed limit of the camera, it is necessary to apply a modulated excitation with pulse durations of the order of the triplet lifetime and synchronize it with the detection. Even so, the resulting dead time between the pulses is much higher than the triplet lifetime, such that most molecules return to the singlet ground state and are re-excited with the next pump pulse without passing to the triplet state. As a result, the observed fluctuations would be very weak and barely detectable. To overcome this issue, a special excitation modulation scheme 121 with synchronized detection 122, as illustrated in FIG. 6, is applied to populate the triplet state 124 and probe the proportion of molecules remaining in the singlet state with a probe pulse 125 of the order of the triplet lifetime. The population of the triplet state 124 is done during the readout 127 of the camera with a pre-pulse 123 prior to the exposure 126. The camera needs to have a fast charge clearing 128 (compared to the triplet lifetime) just before the exposure 126. Due to the lack of a pre-pulse, the first frame 129 shows only a weak triplet population and should be omitted from the final image sequence.

An example wide-field implementation of this technique is shown in FIG. 7. An acousto- or electro-optical modulator 134 is used to generate the pulse sequence in the excitation beam 135. A function generator 132 controls the modulator and triggers the camera 141 according to the modulation scheme illustrated in FIG. 6. The excitation beam 135 is focused in the back aperture of the objective 136 and is directed onto a fluorescently labelled sample 137. Some of the emitted fluorescence 140 is collected by the objective 136, separated and filtered from the excitation by a filter cube 138 and focused onto the array detector of the camera 141. The camera is linked to a computer 131, which is also used for data processing.

The small number of photons collected during the short probe pulse is insufficient to perform localization microscopy but it should be sufficient for cumulant microscopy.

An alternative implementation to capture the triplet state fluctuations is the use of a time-gated camera combined with either a synchronized modulated excitation or a continuous illumination.

It is also possible to exploit the triplet blinking in a confocal detection scheme, where for every scanning point a time trace is recorded. State-of-the-art single point photo-detectors (e.g. avalanche photodiodes) provide the necessary speed to capture the triplet blinking directly, which waives the need for a modulated excitation scheme.

Embodiment 5

Excitation-Induced Fluctuations

In order to expand the range of suitable probes, stochastic fluctuations may also be induced via a fluctuating excitation. Hereto, a varying speckle illumination shall be generated (e.g. by a diffuser plate mounted on a motorized rotation stage), which imposes stochastic intensity fluctuations in the specimen. Because the size of speckles is diffraction-limited, the fluctuations of closely spaced emitters are correlated and hence the resolution is also diffraction-limited. However, if we take advantage of non-linear effects, e.g. exploiting any reversibly saturable optical transition, either the bright or the dark regions can become smaller than a diffraction-limited spot and hence the spatial extent of correlated excitation fluctuations shrinks accordingly.

Embodiment 6

Continuous Cumulation with Hardware Support

In principle, the calculation of cumulants requires access to the entire time series of recorded images, which means that the cumulants can only be evaluated a posteriori—once the recording is complete. This embodiment describes a method for calculating cumulants by processing the captured images in small time intervals, which allows updating and displaying the cumulants during the measurement. The result of this continuous (live) processing shall be identical to the evaluation a posteriori.

The cumulant $\kappa_n$ of order n is obtained as a linear combination of products formed from partial products. These partial products are estimated temporal averages $$\overline{P}_s = \left\langle \prod_{i \in s} I(\vec{p}_i, t) \right\rangle_t,$$

where $I(\vec{p}_i, t)$ is the intensity measured at time t on pixel $\vec{p}_i$ and s is a part of partition S. For evaluating the linear combination, the partial products $\overline{P}_s$ have to be known, which prohibits a continuous accumulation in the cumulant $\kappa_n$ itself. A continuous accumulation can only be performed for the partial products $\overline{P}_s$ required for $\kappa_n$. The linear combination has to be re-evaluated each time an update of $\kappa_n$ is requested.

The method is implemented as follows (the flowchart in FIG. 8 lists the main steps):
(1) the captured images from the camera 151 are transferred to and stored in a memory buffer 152.
(2) The buffered images are processed 153 from time to time by updating the partial products $P_s$ in which the aggregate values of all captured images are accumulated 154.
(3) Each time step 2 completes, the cumulant $\kappa_n$, 155 is re-evaluated based on $\overline{P}_s = P_s/K$ where K is the number of yet accumulated images.
(4) An update of $\kappa_n$ or of derived parameters is displayed 156.
(5) A control task manages and synchronizes the actions of the hard- and software implied in steps 1 to 4.
(6) The user interacts with this control task by a user interface.

Step 2 implies many but simple multiplications and additions of integer values. These calculations have to be performed timely in order to process the images at least as fast as the camera captures them. A possible embodiment outsources this processing to a dedicated hardware module, an FPGA board or a powerful graphics processor (GPU) 153 for instance. This very same module may be used to receive the images from the camera directly (step 1), i.e. by bypassing the shared resources of the computer. This is particularly interesting for calculating higher order cumulants, as the required memory throughput and the required processing speed quickly increase.

Embodiment 7

Widefield Multi-Focal Plane Acquisition and 3D Cross-Cumulation

As described in PCT/US2010/037099, cross-cumulants can be used to increase the pixel grid density, so that the final resolution is not limited by the effective pixel size. Cross-cumulation can be performed in any spatial direction, including the axial dimension, resulting in up to $n^3$ times the original number of pixels. To maximize speed and field-of-view it makes sense to over-sample the system's PSF just as much as needed to satisfy Shannon's sampling theorem (Shannon, C. E. Proc. *I.R.B.*, vol. 37, pp. 10-21, 1949) and to ensure a correlated signal for individual emitters with the specific pixel combinations used in the cross-cumulants (depending on the signal-to-noise ratio). In general, the more pixels are acquired in parallel, the faster is the overall image acquisition. It is thus advantageous to use a widefield imaging system with a high pixel-count camera sensitive and fast enough to detect the emitters' fluctuations.

For widefield 3D cumulant microscopy, instead of acquiring the axial sections sequentially, it is possible to acquire multiple depth or focus planes in parallel using a special detection scheme. The benefit of a parallel depth acquisition is a better exploitation of the available photon budget (especially if the emitters suffer from bleaching) when illuminating the whole sample depth. Furthermore, the resulting contrast of the 3D cross-cumulants as compared to sequentially applied 2D cross-cumulants is expected to be more homogeneous along the optical axis, due to the fact that the fluctuations are stochastic and thus the cumulant response of a single emitter might change with the time and the sequentially acquired depth sections. The eventually imbalanced cumulant contrast might be problematic for a 3D Fourier reweighting (Dertinger et al., Opt. Express 2010) or a cumulant balancing as described in Embodiment 1.

FIG. 9 describes a possible and arbitrarily expandable detection scheme for a parallel acquisition of multiple focal planes or focal channels. It consists of a widefield detection system (161 would be in the infinity path of the microscope) that provides the access to an intermediate image plane via some relay optics 162 for introducing an adjustable field stop 163, m diagonally arranged 50/50 beamsplitters 165 after the tube lens 164 and 2m-2 adjustable mirrors (166 and 167) with two angular degrees of freedom and half of them 167 providing an additional translational (along the optical axis) degree of freedom, as well as 2 cameras (168 and 169) with one being displaceable along the axis 168. By displacing the mirrors and one camera along the optical axis, it is possible to set up $2^m$ distinct optical path lengths with respect to the tube lens and thus probe $2^m$ distinct focal planes. The angular degrees of freedom of the mirrors 166 and 167 are used to arrange the focal planes next to each other such that they fit on the camera sensors 170. The distance between the planes should not exceed half the axial resolution of the imaging system to comply with Shannon's sampling theorem. The field stop 163 ideally has a rectangular, size-adjustable form and is used to avoid cross talk among the channels.

If the emitters blink fast with respect to the camera frame-rate, it might be necessary to use a zero time lag for the calculation of cumulants to ensure a signal from single emitters. Cross-cumulants then present significant advantages over auto-cumulants concerning the elimination of noise. It is thus advantageous to use only pixel combinations without repetitions (see Geissbuehler et al., Biomed. Opt. Express 2011). FIG. 10 shows possible pixel combinations for computing a 3D fourth-order cross-cumulant with a 64-fold increase in pixel count. The acquired intensity time traces of pixels from two distinct focal planes or channels (181 and 182, denoted by a single letter with respectively without an apostrophe to distinguish between the two focal planes) are combined in cross-cumulants to generate inter-pixels 183 in between the original pixel matrix.

Instead of a combination of multiple beamsplitters and mirrors to generate multiple focal planes as described above, it is also possible to achieve a grid arrangement of multiple focal planes on a single camera using a specifically designed phase or amplitude mask placed in a Fourier plane conjugated to the back-aperture of the objective (i.e. before the tube lens 164).

Embodiment 8

Multi-Colour Cumulant Microscopy Using Spectral Cross-Cumulation

In the following paragraphs, we provide a generalized concept for spectrally unmixing multiple emitter species using cumulants.

If the detection arm of the imaging setup contains at least one spectral splitter (e.g. dichroic mirror), which divides the detection beam into two or more spectrally distinct beams that are focused onto two or more distinct detectors or detection areas, cumulant microscopy can also be applied to multi-colour specimens containing multiple, spectrally distinct emitter species.

In the simplest case, a single spectral beam splitter is used to generate two detection channels ($C_1$ and $C_2$) with specific spectral response curves. FIG. 11 shows an example with a single spectral beam splitter 193 and two detector channels $C_1$ [194] and $C_2$ [195] resulting in the spectral response curves $s_1$ and $s_2$ [196]. Let m be the number of distinct emitter species with distinct emission spectra (197 in FIG. 11) that fluctuate stochastically and independently. For the distinction of several emitter species using spectral cross-cumulants, the emission spectra should have an overlap with both spectral response curves of the detection channels. Due to the additivity, the cumulant of multiple independent species corresponds to the sum of the cumulants of each individual species:

$$\kappa_n \left\{ \sum_{i=1}^{m} I_i(\vec{p}, t) \right\}_t = \sum_{i=1}^{m} \kappa_n \{I_i(\vec{p}, t)\}_t,$$

with $I_i(\vec{p},t)$ being the intensity distribution of emitter species i measured on pixel $\vec{p}$ over time t.

A calibration is needed before starting multi-colour imaging experiments. To this end, the relative, ratio-metric intensity response of the two channels ($R_i = I_{C_2,i}/I_{C_1,i}$) is measured for each single emitter species under similar conditions as the envisaged experiments. In the example of FIG. 11, estimating from 196 and 197, the ratios would correspond to $R_1=0.6$ and $R_2=7$. Next, we compute spectral cross-cumulants of order n, which involve u pixels from channel $C_1$ and (n−u) pixels from channel $C_2$. The involved pixels have to probe spatially overlapping detection volumes in the object space. The result of this spectral cross-cumulation can be interpreted as $$\kappa_{n;C_1^u C_2^{n-u}}(\vec{p}) = \sum_{i=1}^{m} R_i^{n-u} \kappa_n \{I_{i;C_1}(\vec{p}, t)\}_t,$$

where $I_{i;C_1}(\vec{p},t)$ stands for the intensity distribution of the isolated species i measured on detector channel $C_1$.

To extract the unknown cumulants of the individual emitter species $\kappa_n\{I_{i;C_1}(\vec{p},t)\}_t$, it is sufficient to compute m spectral cross-cumulants with distinct combinations of pixels to generate a linear equation system, which is then solved for the m unknown cumulants. For example, the following equation system $$\begin{bmatrix} R_1^{n-1} & R_2^{n-1} & \cdots & R_m^{n-1} \\ R_1^{n-2} & R_2^{n-2} & \cdots & R_m^{n-2} \\ \vdots & \vdots & \vdots & \vdots \\ R_1^{n-m} & R_2^{n-m} & \cdots & R_m^{n-m} \end{bmatrix} \begin{bmatrix} \kappa_n\{I_{1;C_1}(\vec{p},t)\}_t \\ \kappa_n\{I_{2;C_1}(\vec{p},t)\}_t \\ \vdots \\ \kappa_n\{I_{m;C_1}(\vec{p},t)\}_t \end{bmatrix} = \begin{bmatrix} \kappa_{n;C_1^1 C_2^{n-1}}(\vec{p}) \\ \kappa_{n;C_1^2 C_2^{n-2}}(\vec{p}) \\ \vdots \\ \kappa_{n;C_1^m C_2^{n-m}}(\vec{p}) \end{bmatrix}$$

allows to obtain the desired spectral unmixing by matrix inversion:

$$\begin{bmatrix} \kappa_n\{I_{1;C_1}(\vec{p},t)\}_t \\ \kappa_n\{I_{2;C_1}(\vec{p},t)\}_t \\ \vdots \\ \kappa_n\{I_{m;C_1}(\vec{p},t)\}_t \end{bmatrix} = \begin{bmatrix} R_1^{n-1} & R_2^{n-1} & \cdots & R_m^{n-1} \\ R_1^{n-2} & R_2^{n-2} & \cdots & R_m^{n-2} \\ \vdots & \vdots & \vdots & \vdots \\ R_1^{n-m} & R_2^{n-m} & \cdots & R_m^{n-m} \end{bmatrix}^{-1} \begin{bmatrix} \kappa_{n;C_1^1 C_2^{n-1}}(\vec{p}) \\ \kappa_{n;C_1^2 C_2^{n-2}}(\vec{p}) \\ \vdots \\ \kappa_{n;C_1^m C_2^{n-m}}(\vec{p}) \end{bmatrix}$$

In the above development, we assumed that all pixels probe the same position in the object space. However, the concept can easily be adapted for spatially distinct pixel positions by introducing a distance factor that corrects for the decrease in spatial correlation for a given set of pixel positions (in analogy to Dertinger et al., Opt Express 2010).

Obviously, if the emitter species can already be spectrally separated by the detection channels themselves without significant cross talk, the unmixing is provided without the need for spectral cross-cumulation.

The invention claimed is:

1. A method for imaging and analyzing an object labelled with stochastically and independently blinking point-like emitters, said method comprising the following steps:
   acquiring a time series of images from blinking point-like emitters,
   calculating higher-order cumulants from said acquired images from the blinking point-like emitters,
   determining the parameter maps for molecular state lifetimes, amplitude and concentration of said emitters by establishing a multi-state blinking model, expressing several cumulant orders as a function of parameters involved in the parameter maps and solving resulting equations for the parameters,
   obtaining a balanced cumulant by spatially deconvolving the cumulant of order n, by taking then the n-th root and by compensating for weighting factors using the parameter maps of the step of determining, and
   displaying said parameter maps and balanced cumulants to obtain information about structural and/or functional features of the object identified by said blinking point-like emitters.

2. The method according to claim 1 further comprising a step of:
   obtaining at least one of the following spatially variable but temporally constant two-state blinking parameter maps: N(p), A(p), pon(p), Ton(p) and off {p);
   wherein N(p) is a number of particles, A(p) is an amplitude, pon(p) is an on-time ratio, Ton(p) and roff (p) are a lifetime of a bright and a dark state, respectively.

3. The method according to claim 1, further comprising the step of:
   Setting a magnification of an imaging system to oversample a point-spread function with detector pixels of the imaging system and thus enabling a computation of spatio-temporal cross-cumulants showing improved signal-to-noise ratios as compared to temporal auto-cumulants.

4. The method according to claim 1 further comprising the following steps:
   capturing images of the blinking point-like emitters with a camera of an imaging system,
   transferring and storing these captured images in a memory buffer,
   processing the captured and buffered images from time to time by updating partial products ps in which aggregate values of all captured images are accumulated,
   each time the previous step is completed, re-evaluating a cumulant <<-,, based on ~Ps=P K, where K is a number of yet accumulated images,
   displaying an update of <<-,, or of derived parameters,
   managing and synchronizing actions of hard- and software implied in the previous steps, and
   allowing user interactions via a user interface.

5. The method according to claim 1 used for spectral unmixing of multiple, spectrally distinct emitter species of the blinking point-like emitters that fluctuate stochastically and independently, said method further comprising the step of:
   generating two or more detection channels with a distinct spectral response; and
   performing a pre-calibration step by measuring an intensity response of different detection channels for each species, said pre-calibration step followed by multiple combinations of spectral cross-cumulants to unmix the different emitter species by solving a linear equation system.

6. A microscopy system to be used with the method of claim 1, said system comprising:
   a light source,
   sample holding means,
   an illumination arm,
   a detection arm,
   a microscope objective located on said detection arm,
   an image or signal processing unit processing the sequence of images from blinking point-like emitters and determining said parameter maps and balanced cumulants, and
   a display for displaying said parameter maps and balanced cumulants.

7. The microscopy system according to claim 6 for probing fast triplet state fluctuations, involving a matching modulated excitation scheme comprising pre-pulse activation means to populate a dark triplet state followed by a short probe pulse synchronized with a camera exposure or a time-gated detection system combined with a synchronized modulation or continuous illumination scheme; said system further comprising:
   an excitation modulation device in the illumination arm, and
   a controller unit driving said excitation modulation device as well as the camera.

8. The microscopy system according to claim 6 for inducing stochastic fluctuations externally by excitation using a varying structured illumination, said system further comprising a device for generating the varying structured illumination in an object space.

9. A microscopy system to be used with the method of claim 1, which allows for a simultaneous acquisition of multiple focal planes and consequently permits spatio-temporal cross-cumulation in 3D, said system comprising a dedicated detection arm composed of multiple beam splitters to split a collected light into multiple detection channels, multiple adjustable mirrors with one translational degree of freedom for adjusting distinct optical path lengths in an image space and two angular degrees of freedom for directing the channels that are next to each other onto at least one array detector; the system further comprising an additional adjustable field stop, placed at a conjugated image plane, to avoid cross talk among the channels.

10. A microscopy system to be used with the method of claim 5, said system comprising at least one spectral beam splitter which generates two or more detection channels with a distinct spectral response.

11. A microscopy system according to claim 8, wherein the object space is a varying saturated speckle field.

* * * * *